United States Patent [19]

Vanhoof et al.

[11] 4,016,284

[45] Apr. 5, 1977

[54] DERIVATIVES OF 1,3-BENZODIOXOLE, THE PREPARATION AND USE THEREOF

[75] Inventors: Pierre M. Vanhoof; Pierre M. Clarebout, both of Brussels, Belgium

[73] Assignee: A. Christiaens Societe Anonyme, Brussels, Belgium

[22] Filed: Dec. 17, 1974

[21] Appl. No.: 533,558

[30] Foreign Application Priority Data

Dec. 17, 1973 United Kingdom ............ 58292/73

[52] U.S. Cl. .................. 424/282; 260/247.2 A; 260/247.2 B; 260/247.5 H; 260/293.58; 260/326.34; 260/340.5; 424/248.54; 424/267; 424/274; 424/248.56

[51] Int. Cl.$^2$ ........................................ A61K 31/36

[58] Field of Search ................. 260/340.5; 424/282

[56] References Cited

UNITED STATES PATENTS 3,915,969  10/1975  Manghisi ..................... 260/340.5

*Primary Examiner*—Ethel G. Love
*Attorney, Agent, or Firm*—Sughrue, Rothwell, Mion, Zinn & Macpeak

[57] ABSTRACT

This invention relates to new derivatives of 1,3-benzodioxole, namely 2-[N-($R_1$, $R_2$ amino-alkyl or alkanoyl or carbamoyl)]-phenylaminomethyl-1,3-benzodioxole, in which $R_1$ is hydrogen or a lower alkyl group, $R_2$ is a lower alkyl group and $R_1$ and $R_2$ may also form with the attached nitrogen atom a nitrogenous heterocyclic ring.

The new derivatives of 1,3-benzodioxole are valuable therapeutic agents for the treatment of heart arrhythmy.

5 Claims, No Drawings

DERIVATIVES OF 1,3-BENZODIOXOLE, THE PREPARATION AND USE THEREOF

SUMMARY OF THE INVENTION

This invention relates to new derivatives of 1,3-benzodioxole, the preparation and use thereof.

The new derivatives of 1,3-benzodioxole according to this invention may be represented by the following general formula:

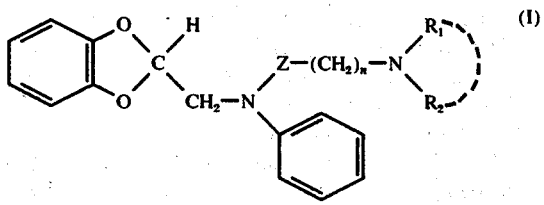

in which Z represents a $-CH_2-$,

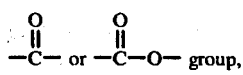

$R_1$ and $R_2$ which may be identical or different represent each a lower alkyl group containing 1 to 4 carbon atoms, $R_1$ may also represent hydrogen, and $R_1$ and $R_2$ may also form with the attached nitrogen atom a nitrogenous heterocyclic ring, $n$ is equal to 1 or 2, when Z represents a $-CH_2-$

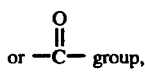

whereas $n$ is equal to 2 or 3, when Z represents a

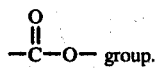

This invention relates also to the acid addition salts of the compounds of formula I.

The nitrogenous heterocyclic ring of the new compounds of formula I may be selected among the piperidino, pyrrolidino and morpholino rings.

The preferred compounds of the formula I are those in which $n$ has the above meanings, $R_1$ and $R_2$ represent a methyl or ethyl group or $R_1$ represents hydrogen whereas $R_2$ represents a methyl or ethyl group or $R_1$ and $R_2$ form together with the attached nitrogen atom a piperidino or pyrrolidino group, as well as the acid addition salts thereof, such as the hydrochlorides, fumarates, oxalates, etc.

This invention relates also to pharmaceutical compositions containing, as active ingredient, at least one compound of the general formula I, together with a pharmaceutically acceptable carrier.

Finally, the invention relates to a process for preparing the new compounds of formula I.

Examples of preferred compounds of formula I are as follows:

-2-[N-(β-ethylaminopropionyl)]-phenylaminomethyl-1,3-benzodioxole (formula I:

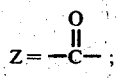

$n = 2$; $R_1 = H$; $R_2 = -C_2H_5$);

-2-[N-(γ-ethylaminopropyl)]-phenylaminoethyl-1,3-benzodioxole (formula I: $Z = -CH_2-$; $n = 2$; $R_1 = H$; $R_2 = -C_2H_5$);

-2-[N-(γ-diethylaminopropyl)]-phenylaminomethyl-1,3-benzodioxole (formula I: $Z = -CH_2-$; $n = 2$; $R_1 = R_2 = -C_2H_5$);

-2-[N-(β-diethylaminoethyl)]-phenylaminomethyl-1,3-benzodioxole (formula I: $Z = -CH_2-$; $n = 1$; $R_1 = R_2 = -C_2H_5$);

-2-[N-(β-dimethylaminoethyl)]-phenylaminomethyl-1,3-benzodioxole formula I: $Z = -CH_2-$; $n = 1$; $R_1 = R_2 = -CH_3$);

-2-[N-(β-piperidinopropionyl)]-phenylaminomethyl-1,3-benzodioxole (formula I:

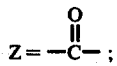

$n = 2$;

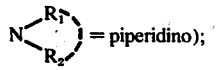

-2-[N-(γ-diethylaminopropylcarbamate)]-phenylaminomethyl-1,3-benzodioxole (formula I:

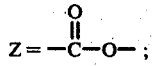

$n = 3$; $R_1 = R_2 = -C_2H_5$).

DETAILED DESCRIPTION OF THE INVENTION

It has been surprisingly found that the compounds of the general formula I are very active for the treatment of heart arrhythmia.

Said compounds can be used for the treatment of various heart diseases such as premature heart contractions, ventricular and supraventricular tachycardias either idiopathic or subsequent to a cardiopathia or to a coronary disease, cardiac arrhythmias due to digitalin intoxication, as well as atrial fibrillation and flutter, particularly in the early stage.

It is known (see Koch-Weser, J. Arch. Int. Med. 129; 763, 1972) that none of the presently available antiarrhythmic agents are satisfactory for the prophylaxis of tachycardias and fibrillation of ventricular origin.

The oral activity of the known antiarrhythmic agents, such as procainamide or lidocaine, is either too short leading to multiple day and night administration (for example with procainamide) or too low to be of some practical utility (for example with lidocaine) or their therapeutic activity is conjugated with frequent and dangerous side effects, such as hypotension (with procainamide), sudden death, agranulocytosis or idiosyncrasy.

The compounds of general formula I according to this invention are very active when orally administered, although they may also be administered parenterally. They have also a long activity duration and are not depressant for the myocardial function.

Applicants do not know any orally active antiarrhythmic agent which does not act at the same time as a depressant of the myocardial function.

The oral antiarrhythmic activity of the compounds of formula I has been proved by tests on rats using aconitine which is a compound causing premature heart contractions and death of the animals.

The method used for these tests is described hereafter:

Animals:
Male or female rats with a body-weight ranging from 380 to 450 g.

Aconitine solution:
3.12 µg aconitine nitrate/1 ml physiological saline.

Solution of the compound to be tested:
0.75% in distilled water.

The relative activity between a tested compound and a reference substance (lidocaine, procainamide) is computed in the following way:

$$A(x) = \frac{\overline{X} - \overline{C}}{\overline{R} - \overline{C}} \times 100$$

where:
$A(x)$ = activity of tested compound X (in %)
$\overline{X}$ = mean dose of aconitine in the animals treated by compound X
$\overline{C}$ = mean dose of aconitine injected in the untreated animals (controls)
$\overline{R}$ = mean dose of aconitine injected in the animals treated by the reference substances.

The following table gives the results of the evaluation of the antiarrhythmic activity by oral route of a great number of acid addition salts of compounds of formula I, compared to the activity of two well known antiarrhythmic agents (procainamide and lidocaine).

TABLE I

| Compound of example | Z | Formula I n | $N{<}^{R_1}_{R_2}$ | Activity in % compared with Lidocaine | Procainamide |
|---|---|---|---|---|---|
| 2 | CH$_2$ | 2 | monoethylamino | 296 | 397 |
| 4 | CH$_2$ | 1 | diethylamino | 417 | 532 |
| 6 | CO | 2 | piperidino | 210 | 268 |
| 7 | COO | 3 | diethylamino | 886 | 1131 |
| 1 | CO | 2 | monoethylamino | 763 | 974 |
| 5 | CH$_2$ | 1 | dimethylamino | 652 | 833 |
| 3 | CH$_2$ | 2 | diethylamino | 866 | 1105 |

The compounds of the formula I may be administered orally or parenterally.

Oral preparations may be administered under the form of capsules, tablets, pills and the like. Each capsule, tablet or pill may contain from 10 to 200 mg of a compound of formula I as active ingredient, together with pharmaceutically acceptable excipients or carriers.

Parenteral preparations may consist in a solution for perfusion or for intravenous or intramuscular injection. Such a solution may contain from 0.2 per thousand to 2 per thousand of a compound of formula I.

The parenteral preparation may be either a solution which may be directly used for the perfusion and contains a proportion of the active ingredient within the above limits, or a concentrated solution containing 1 to 10% of the active ingredient, said concentrated solution being diluted when administered to a patient.

The initial dose of active ingredient may be of 200 to 800 mg per day during 2 or 3 days, the maintenance dose being of about 25 mg to 300 mg per day.

If a single dose is sufficient for obtaining the therapeutic effect, this dose is generally comprised between 50 and 300 mg.

The active ingredient may be administered at the same time by the parenteral route (for example by perfusion) and by oral route.

This invention relates also to a process for preparing the new compounds of formula I.

The process according to this invention comprises generally the conversion of a compound of the formula:

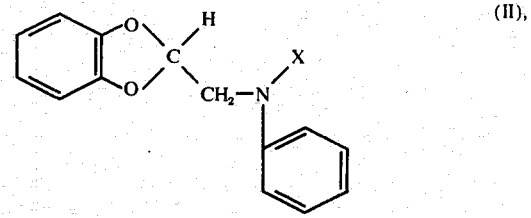

in which X represents hydrogen or a COCl group into a compound of the formula I by aminoalkylation or aminoalkanoylation, the obtained compound of formula I being converted, if desired, into an acid addition salt in a manner known per se.

The aminoalkylation or aminoalkanoylation of a compound of formula II, into a compound of formula I may be effected in one or several steps.

According to one embodiment of said process, 2-phenylamino-methyl-1,3-benzodioxole of the formula

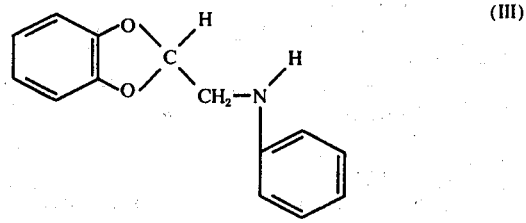

is reacted wwith an amino compound of the formula

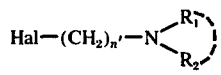 (IV)

in which $n' = 1$, 2 or 3 and Hal is a halogen atom, in the presence of sodium amide, so as to obtain, in one step, a compound of formula I, in which Z represents a —CH$_2$ group, $n = 1$ or 2 and R$_1$ and R$_2$ have the above meanings.

According to another embodiment of the process according to this invention, 2-phenylamino-methyl-1,3-benzodioxole is converted into a compound of formula I in two steps, the first step comprising the reaction of 2-phenylamino-methyl-1,3-benzodioxole wwith compound of the formula:

 (V), in which $n' = 1$, 2 or 3 and Hal is a halogen atom, so as to obtain a compound of the formula

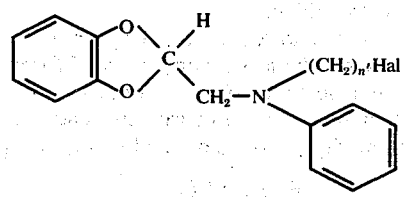 (VI)

the second step comprising the reaction of the compound of formula VI, with an amine of the formula

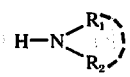 (VII)

in which R$_1$ and R$_2$ have the above meanings, so as to obtain a compound of formula (I), in which Z represents a —CH$_2$ group, $n = 1$ or 2 and R$_1$ as well as R$_2$ have the above meanings.

According to still another embodiment of the process according to the invention, 2-phenylamino-methyl-1,3-benzodioxole is converted into a compound of formula I in two or three steps, the first step comprising the reaction of 2-phenylamino-methyl-1,3-benzodioxole with an acid halide of the formula Hal (CH$_2$)$_n$, CO Hal   (VIII)

in which $n' = 1$ or 2 and Hal is a halogen atom, so as to obtain an acylated compound of the formula:

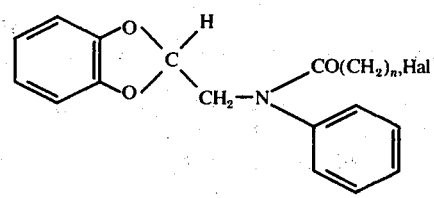 (IX)

the second step comprising the reaction of the acylated compound of formula IX with an amine of the formula

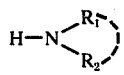 (VII)

so as to obtain a compound of formula I, in which Z represents a $$-\overset{O}{\underset{\|}{C}}- \text{ group,}$$

$n$ is equal to 1 or 2 and R$_1$ as well as R$_2$ have the above meanings, i.e. a compound of the following formula:

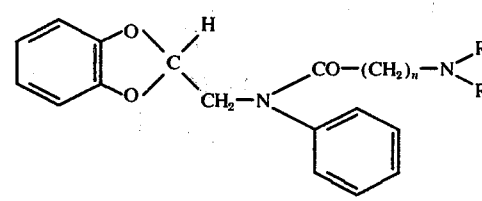 (X)

When it is desired to obtain a compound of formula I, in which Z represents a —CH$_2$— group, $n = 1$ or 2 and R$_1$ as well as R$_2$ have the above meanings, the process comprises a third step consisting in reducing a compound of formula X, for example by means of lithium aluminium hydride.

According to another embodiment of the process of this invention, the compounds of the formula I, in which Z represents a $$-\overset{O}{\underset{\|}{C}}-O- \text{ group,}$$

$n = 2$ or 3 and R$_1$ and R$_2$ have the above meanings, may be obtained from a compound of the formula II, in which X represents $$-\overset{O}{\underset{\|}{C}}-Cl \text{ group,}$$

in one step, by reacting said compound with a compound of the formula

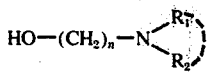 (XI)

in which $n$, R$_1$ and R$_2$ have the above meanings.

According to another embodiment of the process according to this invention, the compounds of the formula I, in which Z represents a $$-\overset{O}{\underset{\|}{C}}-O- \text{ group,}$$

whereas $n$, R$_1$ and R$_2$ have the above meanings, may also be obtained from a compound of the formula II, in which X represents a

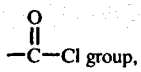
—C—Cl group, by two steps, the first step comprising the reaction of said compound with a compound of the formula

HO—(CH$_2$)$_{n'}$—Cl     (XII), in which $n' = 2$ or $3$, so as to obtain a compound of the formula

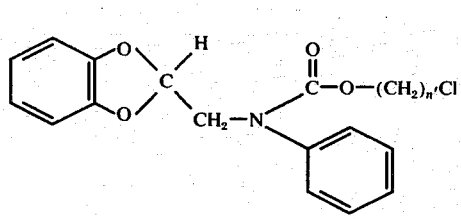
(XIII)

in which $n'$ has the above meanings, and the second step comprising the reaction of the compound of the formula XIII with an amine of the formula

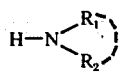
VII in which R$_1$ and R$_2$ have the above meanings.

The 2-phenylamino-methyl-1,3-benzodioxole is a new compound which may be prepared from an ester of 1,3-benzodioxole-2-carboxylic acid, particularly from ethyl 1,3-benzodioxole-carboxylate which is a known compound of the formula:

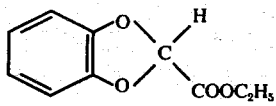
(XIV)

described by Howard, Hartzfeld, Johnson and Gilman, J.O.C. 22, 1717 (1957), by the following process:

1. Reduction of ethyl 1,3-benzodioxole-2-carboxylate into 2-hydroxymethyl-1,3-benzodioxole of the following formula:

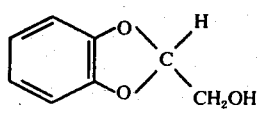
(XV)

this reaction being effected, for example, by means of lithium aluminium hyride (AlLiH$_4$) in ether. The obtained product boils at 90°–92° C under a pressure of 0.5 mm.

Conversion of the 2-hydroxymethyl-1,3-benzodioxole of formula III into the mesylate thereof of the following formula:

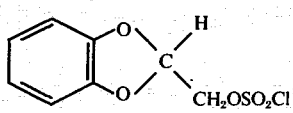
(XVI)

by reaction with mesyl chloride (CH$_3$SO$_2$Cl)

3. Conversion of the mesylate of formula V into 2-phenylaminomethyl-1,3-benzodioxole of the following formula

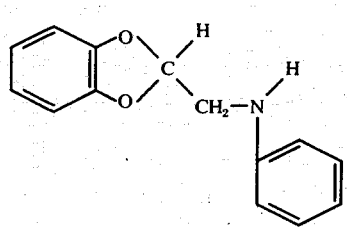
(III)

by reaction with aniline.

The carbamoyl chloride of 2-phenylamino-methyl-1,3-benzodioxole, which is a compound of formula II, in which X represents a —COCl group, is also a new compound which may be prepared by reaction of 2-phenylamino-methyl-1,3-benzodioxole with phosgene.

EXAMPLES

The following examples illustrate the preparation of the new compounds of formula I.

Example 1

Preparation of
2-[N-(β-ethylaminopropionyl)]-phenylaminomethyl-1,3-benzodioxole (formula I:

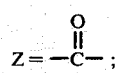

$n = 2$; R$_1$ = H; R$_2$ = —C$_2$H$_5$)

1. Preparation of the mesylate of 2-hydroxymethyl-1,3-benzodioxole (formula XVI)

To a solution of 17.8 g of 2-hydroxymethyl-1,3-benzodioxole in 60 ml of pyridine, 10 ml of mesyl chloride are added drop by drop at a temperature comprised between 0° C and —5° C. The obtained mixture is stirred during 1 hour at room temperature and then poured onto water and ice. After filtration, the filtrate is extracted with ether and dried. The desired product crystallizes when the dried ether solution is concentrated and petroleum ether (B.P. 40°–60° C) is added thereto. The obtained mesylate (22.2 g - yield: 83%) melts at 64°–66° C.

Analysis: % calculated: C 46.96; H 4.38; S 13.9. % found: C 46.7; H 4.29; S 13.7.

Preparation of 2-phenylaminomethyl-1,3-benzodioxole (formula III)

14 g of the mesylate of formula V and 60 ml of aniline are heated and stirred during 4 hours at 135° C. After cooling, 200 ml of ether are added and the formed aniline mesylate is removed. The ether and the free aniline are then removed and the residue is treated with 200 ml of ether. After filtration, a gaseous stream of hydrochloric acid is bubbled into the filtrate. The product is recrystallized from petroleum ether. M.P. 70°–72° C. Yield: 88%.

Analysis: % calculated: C 73.99; H 5.76; N 6.16; % found: C 73.6; H 5.67; N 6.00

3. Preparation of 2-[N-(β-chloropropionyl)]-phenylaminomethyl-1,3-benzodioxole (formula IX: $n = 2$).

14 g of the hydrochloride of 2-phenylaminomethyl-1,3-benzodioxole, 7.37 g (5.6 ml) of Cl—CO—(CH$_2$)$_2$Cl and 30 ml of benzene are refluxed during 3 hours. The obtained liquid is concentrated to dryness and then extracted with water. After alkalinization, the aqueous solution is extracted with chloroform. The chloroform solution is dried and filtered. After removal of the chloroform, an oil is obtained which is directly used in the following step.

4. Preparation of the hydrochloride of 2-[N-(β-ethylaminopropionyl)]-phenylaminomethyl-1,3-benzodioxole. (formula I:

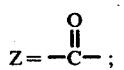

$n = 2$; $R_1 = H$ and $R_2 = -C_2H_5$).

5 g of 2-[N-(β-chloropropionyl)]-phenylaminomethyl-1,3-benzodioxole, 37 ml of an alcoholic solution of ethylamine (0.125 mol; 15.3 g/100 ml) are heated in an autoclave at 95° C during 17 hours. After cooling and removal of the solvent, the residue is treated with water, made alkaline and extracted with chloroform. The chloroform solution is dried and concentrated to dryness. 100 ml of anhydrous ether are added to the residue and a stream of gaseous hydrochloric acid is bubbled into the ether solution. The obtained oil is crystallized in ether. After recrystallization from acetone, the desired product melts at 110° – 112° C.

Analysis: % calculated: C 62.88; H 6.38; N 7.72; Cl 9.77, % found: C 62.42; H 6.39; N 7.77; Cl 9.68.

EXAMPLE 2

Preparation of the hydrochloride of 2-[N-(γ-ethylaminopropyl)]-phenylaminomethyl-1,3-benzodioxole (formula I: $Z = -CH_2-$; $n = 2$; $R_1 = H$; $R_2 = -C_2H_5$).

First method:

2.49 g of 2-phenylaminomethyl-1,3-benzodioxole (formula III) dissolved in 50 ml of toluene are refluxed under nitrogen during 15 minutes, in the presence of 1.25 g of sodium amide.

5.28 g of the hydrobromide of 1-bromo-3-ethylaminopropane are then added and the mixture is refluxed during 24 hours. After cooling, 75 ml of water are added. After decantation, the aqueous phase is extracted by means of toluene. The toluene phase is extracted with 2N hydrochloric acid. The pH is adjusted to 6 and the mixture is extracted with chloroform. The chloroform solution is dried and the chloroform then removed. The residue is recrystallized from acetone and ether. M.P. 112° – 113° C.

Analysis: % calculated: C 65.4; H 7.22; N 8.02; Cl 10.16, % found: C 65.2; H 7.16; N 8.03; Cl 10.3.

Second method:

1. Preparation of the hydrochloride of 2-[N-(γ-chloropropyl)]-phenylaminomethyl-1,3-benzodioxole (formula VI: $n = 3$).

15.34 g of 2-phenylaminomethyl-1,3-benzodioxole, 52.3 g of 1-bromo-3-chloropropane, 70 ml of isopropanol and 27.64 g of potassium carbonate are refluxed during 24 hours. After cooling, 300 ml of water are added and the obtained solution is extracted with dichloroethane. After drying, the dichloroethane and the excess of 1-bromo-3-chloropropane are removed. The residue is treated with ethyl acetate and a stream of gaseous dry hydrochloric acid is caused to pass through the obtained solution. After filtration, the filtrate is concentrated to dryness, so as to obtain the hydrochloride of 2-[N-(γ-chloropropyl)]-phenylaminomethyl-1,3-benzodioxole. M.P. 115° – 117° C.

2. Preparation of the hydrochloride of 2-[(β-ethylaminopropyl)]-phenylaminomethyl-1,3-benzodioxole.

8 g of the compound of formula XIII and 0.184 mole of ethylamine dissolved in ethanol are heated in an autoclave at 95° C during 20 hours. The desired hydrochloride is obtained with a yield of 90%. M.P. 112° – 113° C.

EXAMPLE 3

Preparation of the hydrochloride of 2-[N-(γ-diethylaminopropyl)]-phenylaminomethyl-1,3-benzodioxole.

(formula I: $Z = CH_2$; $n = 2$; $R_1 = R_2 = -C_2H_5$).

This compound is prepared as described in the first method of example 2, using the hydrochloride of 1-chloro-3-diethylaminopropane instead of the hydrobromide of 1-bromo-3-ethylaminopropane.

The hydrochloride recrystallized from acetone melts at 126° – 128° C.

Analysis: % calculated: C 66.91; H 7.75; N 7.43; Cl 9.41, % found: C 66.85; H 7.74; N 7.70; Cl 9.36.

EXAMPLE 4

Preparation of the fumarate of 2-[N-(β-diethylaminoethyl)]-phenylaminomethyl-1,3-benzodioxole (formula I: $Z = CH_2$; $n = 1$; $R_1 = R_2 = -C_2H_5$).

This compound is prepared as described in example 2 using β-chloroethyl-diethylamine as alkylating agent.

The fumarate is recrystallized from ethanol. M.P. 134° – 135° C.

Analysis: % calculated: C 65.14; H 6.83; N 6.33. % found: C 64.90; H 6.79; N 6.45.

EXAMPLE 5

Preparation of the hydrochloride of 2-[N-(β-dimethylamino)]-phenylaminomethyl-1,3-benzodioxole (formula I: $Z = CH_2$; $n = 1$; $R_1 = R_2 = -CH_3$).

This compound is prepared as described in example 2 using β-chloroethyldimethylamine as alkylating agent.

The hydrochloride melts at 154° – 156° C after recrystallization from acetone.

Analysis: % calculated: C 64.56; H 6.92; N 8.36; Cl 10.58. % found: C 64.53; H 6.91; N 8.59; Cl 10.71.

EXAMPLE 6

Preparation of the fumarate of 2-[N-(β-piperidinopropionyl)]-phenylaminomethyl-1,3-benzodioxole (formula I:

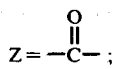

n = 2;

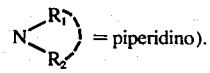

8.8 g of 2-[N-(β-chloropropionyl)]-phenylaminomethyl-1,3-benzodioxole and 5.1 g of piperidine are refluxed in 90 ml of ethanol during 24 hours. After removal of the alcohol and of the excess of piperidine, 100 ml of 2N hydrochloric acid are added. The obtained solution is filtered, made alkaline and extracted with chloroform. After drying, the chloroform solution is concentrated to dryness. The fumarate is then prepared in aqueous solution. The aqueous solution is evaporated and the residue is recrystallized from a mixture of acetone and methanol. M.P. 169°–170° C.

Analysis: % calculated: C 64.71; H 6.26; N 5.80. % found: C 64.9; H 6.21; N 5.86.

EXAMPLE 7

Preparation of the oxalate of γ-diethylaminopropylcarbamate of 2-phenylaminomethyl-1,3-benzodioxole.

(formula I:

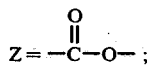

n = 3; $R_1 = R_2 = -C_2H_5$).

1. Preparation of the carbamyl chloride of 2-phenylaminomethyl-1,3-benzodioxole (formula II: X = —COCl)

4 g of 2-phenylaminomethyl-1,3-benzodioxole, 80 ml of benzene and 100 ml of a toluene solution of phosgene are refluxed during 5 hours. After removal of the solvents, the residue is recrystallized from petroleum ether. M.P. 86°–87° C.

Analysis: % calculated: C 62.18; H 4.17; N 4.83; Cl 12.23. % found: C 62.21; H 4.19; N 4.99; Cl 12.30.

2. Preparation of γ-chloropropylcarbamate of 2-phenylaminomethyl-1,3-benzodioxole (formula XII: n = 3)

4.25 g of the carbamoyl chloride of 2-phenylaminomethyl-1,3-benzodioxole and 7 ml of 1-hydroxy-3-chloropropane are stirred and heated during 6 hours at 110° C. After filtration, the solution is concentrated to dryness. The obtained product is directly used in the following step.

3. Preparation of γ-diethylaminopropylcarbamate of 2-phenylaminomethyl-1,3-benzodioxole 4.1 g of γ-chloropropylcarbamate of 2-phenylaminomethyl-1,3-benzodioxole, 17 ml of diethylamine, 17 ml of anhydrous ethanol and 0.4 g of sodium iodide are stirred and heated in an autoclave at 95° C during 24 hours. After cooling and filtration, the solution is concentrated so as to remove the volatile materials and the residue is treated with 50 ml of 2N hydrochloric acid. The obtained solution is made alkaline and extracted with chloroform. After drying of the organic phase and evaporation, the residue is converted into oxalate, which is recrystallized from acetone.

Analysis: % calculated: C 60.75; H 6.17; N 5.9. % found: C 61; H 6.44; N 6.1.

What we claim is:

1. Derivatives of 1,3-benzodioxole of the following general formula:

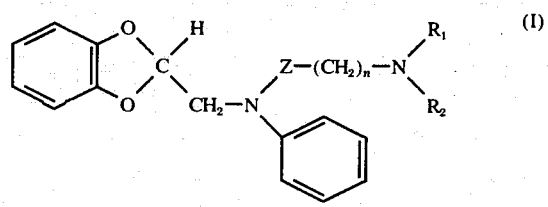

in which Z represents —CH$_2$—, R$_1$ and R$_2$ which may be identical or different represent each a lower alkyl group containing 1 to 4 carbon atoms, and R$_1$ may also represent hydrogen, n is equal to 1 or 2 and the pharmaceutically acceptble acid addition salts thereof.

2. Derivatives of 1,2-benzodioxole according to claim 1, wherein both R$_1$ and R$_2$ represent a methyl or ethyl group, and the pharmaceutically acceptable acid addition salts thereof.

3. Derivatives of 1,3-benzodioxole according to claim 1, wherein R$_1$ represents hydrogen and R$_2$ represents a methyl or ethyl group, and the pharmaceutically acceptable acid addition salts thereof.

4. Derivatives of 1,3-benzodioxole according to claim 1, wherein R$_1$ represents —C$_2$H$_5$; R$_2$ represents —C$_2$H$_5$; n represents 2; and Z represents —CH$_2$—.

5. A pharmaceutical composition for the treatment of heart arrhythmia which comprises as the active ingredient an amount effective to treat heart arrhythmia of a derivative according to claim 1 together with a pharmaceutical excipient.

* * * * *